United States Patent
Sun

(10) Patent No.: US 12,015,860 B2
(45) Date of Patent: Jun. 18, 2024

(54) ACTIVE PIXEL CIRCUIT AND METHOD FOR CONTROLLING THE SAME, AND ACTIVE PIXEL SENSING DEVICE

(71) Applicants: BEIJING BOE TECHNOLOGY DEVELOPMENT CO., LTD., Beijing (CN); BOE TECHNOLOGY GROUP CO., LTD., Beijing (CN)

(72) Inventor: Tuo Sun, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 704 days.

(21) Appl. No.: 17/268,511

(22) PCT Filed: May 20, 2020

(86) PCT No.: PCT/CN2020/091295
§ 371 (c)(1),
(2) Date: Feb. 15, 2021

(87) PCT Pub. No.: WO2020/233599
PCT Pub. Date: Nov. 26, 2020

(65) Prior Publication Data
US 2021/0266480 A1      Aug. 26, 2021

(30) Foreign Application Priority Data
May 21, 2019   (CN) .......................... 201910424162.0

(51) Int. Cl.
*H04N 25/709*      (2023.01)
*A61B 6/42*         (2024.01)
(Continued)

(52) U.S. Cl.
CPC ......... *H04N 25/709* (2023.01); *A61B 6/4208* (2013.01); *H01L 27/14612* (2013.01); *H01L 27/14659* (2013.01); *H04N 25/77* (2023.01)

(58) Field of Classification Search
CPC . H04N 25/709; H04N 25/77; H01L 27/14612
See application file for complete search history.

(56) References Cited

U.S. PATENT DOCUMENTS

2012/0081588 A1    4/2012   Adkisson et al.
2014/0340548 A1   11/2014   Adkisson et al.
(Continued)

FOREIGN PATENT DOCUMENTS

CN        102984473            3/2013
CN        110166671            8/2019
WO    WO-2017197969 A1  * 11/2017  ............. H04N 5/365

OTHER PUBLICATIONS

PCT International Search Report (w/ English translation) for corresponding PCT Application No. PCT/CN2020/091295, dated Aug. 19, 2020, 6 pages.
(Continued)

*Primary Examiner* — Thanh Luu
(74) *Attorney, Agent, or Firm* — Dority & Manning, PA

(57) ABSTRACT

An active pixel circuit includes a photosensitive device, a source follower transistor, and a compensation circuit. The photosensitive device is configured to generate a photocurrent under an irradiation of light rays, and transmit the photocurrent to a first node. A control electrode of the source follower transistor is coupled to a floating diffusion node. The compensation circuit is configured to: transmit a target threshold voltage to the first node, a voltage of the first node being associated with a voltage generated by the photocurrent and the target threshold voltage; store the voltage of the first node; and obtain a compensation voltage according to the voltage of the first node, and output the compensation
(Continued)

voltage to the floating diffusion node. The target threshold voltage is the same as a threshold voltage of the source follower transistor.

15 Claims, 8 Drawing Sheets

(51) Int. Cl.
*H01L 27/146* (2006.01)
*H04N 25/77* (2023.01)

(56) References Cited

U.S. PATENT DOCUMENTS

| | | |
|---|---|---|
| 2017/0180662 A1 | 6/2017 | Chen et al. |
| 2017/0295335 A1 | 10/2017 | Kim |
| 2018/0249109 A1* | 8/2018 | Yang ............... H04N 25/67 |
| 2019/0281242 A1 | 9/2019 | Cheng et al. |
| 2020/0162687 A1 | 5/2020 | Wang |
| 2020/0162688 A1 | 5/2020 | Wang |

OTHER PUBLICATIONS

Chinese First Office Action (w/ English translation) for corresponding CN Application No. 201910424162.0, 13 pages.

* cited by examiner

01

ACTIVE PIXEL CIRCUIT AND METHOD FOR CONTROLLING THE SAME, AND ACTIVE PIXEL SENSING DEVICE

CROSS-REFERENCE TO RELATED APPLICATIONS

This application is a national phase entry under 35 USC 371 of International Patent Application No. PCT/CN2020/091295 filed on May 20, 2020, which claims priority to Chinese Patent Application No. 201910424162.0, filed on May 21, 2019, which are incorporated herein by reference in their entirety.

TECHNICAL FIELD

The present disclosure relates to the field of sensors, and in particular, to an active pixel circuit and a method for controlling the same, and an active pixel sensing device.

BACKGROUND

At present, active pixel sensing devices are widely used in many fields. An active pixel sensing device includes a plurality of active pixel circuits, i.e., active pixel sensor (APS) pixel circuits. The active pixel circuit is capable of converting optical signals into electrical signals, so that a detection result of a detection object can be obtained according to the electrical signals.

SUMMARY

In an aspect, an active pixel circuit is provided. The active pixel circuit includes a photosensitive device, a source follower transistor, and a compensation circuit. The photosensitive device is coupled to a first node. The photosensitive device is configured to generate a photocurrent under an irradiation of light rays, and to transmit the photocurrent to the first node. A control electrode of the source follower transistor is coupled to a floating diffusion node. The compensation circuit is coupled to the first node. The compensation circuit is further coupled to the floating diffusion node, a first control terminal, a second control terminal, a third control terminal, a first reference voltage terminal, a second reference voltage terminal, and a first power supply voltage terminal.

The compensation circuit is configured to: transmit a target threshold voltage to the first node under control of voltages of the first control terminal, the second control terminal, the third control terminal, the first reference voltage terminal, the second reference voltage terminal, and the first power supply voltage terminal, a voltage of the first node being associated with a voltage generated by the photocurrent and the target threshold voltage; store the voltage of the first node; obtain a compensation voltage according to the voltage of the first node; and output the compensation voltage to the floating diffusion node. The target threshold voltage is the same as or substantially the same as a threshold voltage of the source follower transistor.

In some embodiments, the compensation circuit includes a threshold voltage acquisition sub-circuit, a control sub-circuit, and an energy storage sub-circuit. The threshold voltage acquisition sub-circuit is coupled to the first node and the first power supply voltage terminal. The control sub-circuit is coupled to the first node, a second node, the floating diffusion node, the first control terminal, the second control terminal, the third control terminal, the first reference voltage terminal, and the second reference voltage terminal. The energy storage sub-circuit is coupled between the second node and the floating diffusion node.

The threshold voltage acquisition sub-circuit is configured to adjust the voltage of the first node to an associated voltage under the control of the voltage of the first power supply voltage terminal. The associated voltage is associated with the target threshold voltage and the voltage generated by the photocurrent. The control sub-circuit is configured to: output the associated voltage of the first node to the second node and a first reference voltage received at the first reference voltage terminal to the floating diffusion node under the control of the voltages of the first control terminal, the second control terminal, and the third control terminal; and charge the energy storage sub-circuit. The control sub-circuit is further configured to: adjust a voltage of the second node from the associated voltage to a second reference voltage received at the second reference voltage terminal under the control of the voltages of the first control terminal, the second control terminal, and the third control terminal; and adjust a voltage of the floating diffusion node from the first reference voltage to the compensation voltage through the energy storage sub-circuit.

In some embodiments, the threshold voltage acquisition sub-circuit includes a first transistor. A control electrode and a first electrode of the first transistor are coupled to the first power supply voltage terminal, and a second electrode of the first transistor is coupled to the first node. A threshold voltage of the first transistor is the target threshold voltage.

In some embodiments, the control sub-circuit includes a second transistor, a third transistor and a fourth transistor. A control electrode of the second transistor is coupled to the second control terminal, a first electrode of the second transistor is coupled to the first node, and a second electrode of the second transistor is coupled to the second node. A control electrode of the third transistor is coupled to the third control terminal, a first electrode of the third transistor is coupled to the first reference voltage terminal, and a second electrode of the third transistor is coupled to the floating diffusion node. A control electrode of the fourth transistor is coupled to the first control terminal, a first electrode of the fourth transistor is coupled to the second reference voltage terminal, and a second electrode of the fourth transistor is coupled to the second node.

In some embodiments, the energy storage sub-circuit includes a first capacitor. A first electrode of the first capacitor is coupled to the second node, and a second electrode of the first capacitor is coupled to the floating diffusion node.

In some embodiments, the active pixel circuit further includes a plurality of transistors in parallel with the source follower transistor. Characteristics of the plurality of transistors are the same as or substantially the same as characteristics of the source follower transistor.

In some embodiments, the active pixel circuit further includes a row selector transistor. A first electrode of the source follower transistor is coupled to a second power supply voltage terminal, and a second electrode of the source follower transistor is coupled to a first electrode of the selector transistor. A control electrode of the selector transistor is coupled to the first control terminal, and a second electrode of the selector transistor is coupled to a signal output terminal.

In some embodiments, the photosensitive device is a photodiode. An anode of the photodiode is coupled to a bias voltage terminal, and a cathode of the photodiode is coupled to the first node.

In some embodiments, the compensation circuit includes a threshold voltage acquisition sub-circuit, a control sub-circuit, and an energy storage sub-circuit. The threshold voltage acquisition sub-circuit includes a first transistor. The control sub-circuit includes a second transistor, a third transistor and a fourth transistor. The energy storage sub-circuit includes a first capacitor. The active pixel circuit further includes a selector transistor. The photosensitive device is a photodiode.

A control electrode and a first electrode of the first transistor are coupled to the first power supply voltage terminal, and a second electrode of the first transistor is coupled to the first node. A control electrode of the second transistor is coupled to the second control terminal, a first electrode of the second transistor is coupled to the first node, and a second electrode of the second transistor is coupled to a second node. A control electrode of the third transistor is coupled to the third control terminal, a first electrode of the third transistor is coupled to the first reference voltage terminal, and a second electrode of the third transistor is coupled to the floating diffusion node. A control electrode of the fourth transistor is coupled to the first control terminal, a first electrode of the fourth transistor is coupled to the second reference voltage terminal, and a second electrode of the fourth transistor is coupled to the second node.

A first electrode of the first capacitor is coupled to the second node, and a second electrode of the first capacitor is coupled to the floating diffusion node. A first electrode of the source follower transistor is coupled to a second power supply voltage terminal, and a second electrode of the source follower transistor is coupled to a first electrode of the selector transistor. A control electrode of the selector transistor is coupled to the first control terminal, and a second electrode of the selector transistor is coupled to a signal output terminal. An anode of the photodiode is coupled to a bias voltage terminal, and a cathode of the photodiode is coupled to the first node.

In another aspect, a method for controlling the active pixel circuit as described above is provided. In a case where the compensation circuit of the active pixel circuit includes a threshold voltage acquisition sub-circuit, a control sub-circuit, and an energy storage sub-circuit, the method for controlling the active pixel circuit includes a first stage to a third stage.

In the first stage, the photosensitive device generates the photocurrent under the irradiation of light rays, and transmits the photocurrent to the first node. The threshold voltage acquisition sub-circuit adjusts the voltage of the first node to an associated voltage under the control of the first power supply voltage terminal. The associated voltage is associated with the target threshold voltage and the voltage generated by the photocurrent. A turn-off voltage is input to the first control terminal, and turn-on voltages are respectively input to the second control terminal and the third control terminal. The control sub-circuit outputs the associated voltage of the first node to a second node and outputs a first reference voltage received at the first reference voltage terminal to the floating diffusion node under the control of the first control terminal, the second control terminal, and the third control terminal, and charges the energy storage sub-circuit.

In the second stage, turn-off voltages are respectively input to the first control terminal, the second control terminal and the third control terminal. The control sub-circuit maintains a voltage of the second node at the associated voltage and maintains a voltage of the floating diffusion node at the first reference voltage under the control of the first control terminal, the second control terminal and the third control terminal.

In the third stage, a turn-on voltage is input to the first control terminal, and turn-off voltages are respectively input to the second control terminal and the third control terminal. The control sub-circuit adjusts the voltage of the second node from the associated voltage to a second reference voltage received at the second reference voltage terminal under the control of the first control terminal, the second control terminal, and the third control terminal, and adjusts the voltage of the floating diffusion node from the first reference voltage to the compensation voltage through the energy storage sub-circuit.

In yet another aspect, an active pixel sensing device is provided. The active pixel sensing device includes the active pixel circuit(s) as described above.

In some embodiments, the active pixel sensing device includes a plurality of active pixel circuits arranged in an array.

BRIEF DESCRIPTION OF THE DRAWINGS

In order to describe technical solutions in the present disclosure more clearly, accompanying drawings to be used in some embodiments of the present disclosure will be introduced below briefly. Obviously, the accompanying drawings to be described below are merely accompanying drawings of some embodiments of the present disclosure, and a person of ordinary skill in the art may obtain other drawings according to these drawings. In addition, the accompanying drawings to be described below may be regarded as schematic diagrams, and are not limitations on an actual size of a product, an actual process of a method and an actual timing of a signal to which the embodiments of the present disclosure relate.

DETAILED DESCRIPTION

Technical solutions in some embodiments of the present disclosure will be described below dearly and completely in combination with the accompanying drawings. Obviously, the described embodiments are merely some but not all embodiments of the present disclosure. All other embodiments obtained on a basis of the embodiments of the present disclosure by a person of ordinary skill in the art shall be included in the protection scope of the present disclosure.

Unless the context requires otherwise, term "comprise" and other forms thereof such as the third-person singular form "comprises" and the present participle form "comprising" throughout the description and the claims are construed as an open and inclusive meaning, i.e., "included, but not limited to". In the description of the specification, terms such as "one embodiment", "some embodiments", "exemplary embodiments", "example", "specific example" or "some examples" are intended to indicate that specific features, structures, materials or characteristics related to the embodiment(s) or example(s) are included in at least one embodiment or example of the present disclosure. Schematic representations of the above terms do not necessarily refer to the same embodiment(s) or example(s). In addition, the specific features, structures, materials or characteristics may be included in any one or more embodiments/examples in any suitable manner.

Terms such as "first" and "second" are only used for describing purposes, and are not to be construed as indicating or implying the relative importance or implicitly indicating the number of indicated technical features below. Thus, a feature defined as "first" or "second" may explicitly or implicitly include one or more of the features. In the description of the embodiments of the present disclosure, the term "a plurality of" means two or more unless otherwise specified.

In the description of some embodiments, the terms such as "coupled" and "connected" and their extensions may be used. For example, the term "connected" may be used in the description of some embodiments to indicate that two or more components are in direct physical or electrical contact with each other. For another example, the term "coupled" may be used in the description of some embodiments to indicate that two or more components are in direct physical or electrical contact. However, the term "coupled" or "communicatively coupled" may also mean that two or more components are not in direct contact with each other, but still cooperate or interact with each other. The embodiments disclosed herein are not necessarily limited to the content herein.

The use of "applicable to" or "configured to" means an open and inclusive expression, which does not exclude apparatuses that are applicable to or configured to perform additional tasks or steps.

Figure 1:
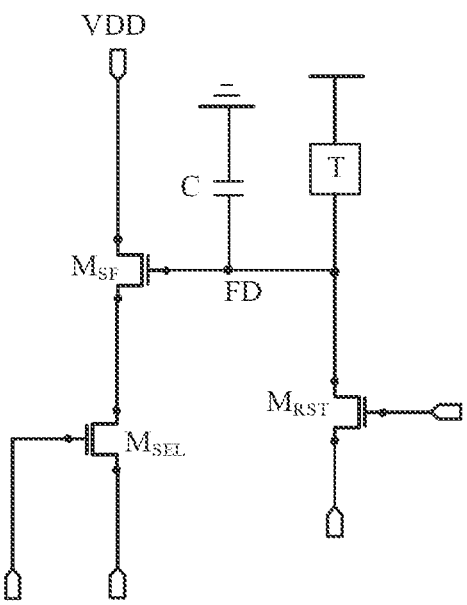
FIG. 1 is a diagram showing a circuit structure of an active pixel circuit in the related art.

In the related art, as shown in FIG. 1, an active pixel circuit includes a photosensitive device T, a capacitor C, a reset transistor $M_{RST}$, a source follower transistor (also called current source follower transistor) $M_{SF}$, a selector transistor (also called row selector transistor) $M_{SEL}$. The photosensitive device T generates a photocurrent under light irradiation, and outputs the photocurrent to a floating diffusion node FD, i.e., a control electrode of the source follower transistor $M_{SF}$. Therefore, a magnitude of the photocurrent is capable of determining a magnitude of a voltage at the floating diffusion node FD, that is, determining a conductivity of the source follower transistor $M_{SF}$, thereby determining a magnitude of a current flowing through the source follower transistor $M_{SF}$. Therefore, a light intensity sensed by the photosensitive device T can be obtained by measuring the magnitude of the current flowing through the source follower transistor $M_{SF}$.

However, due to a deviation of a manufacturing process, and a drift of a threshold voltage of the source follower transistor $M_{SF}$ with an increase of use time, especially to a problem of a poor uniformity of the threshold voltage in a short time for using a low temperature poly-silicon thin film transistor (LTPS TFT) as the source follower transistor $M_{SF}$, unstable and biased detection results and other drawbacks may be caused.

Based on this, the present disclosure provides an active pixel circuit and an active pixel sensing device, to solve the problem of unstable detection results caused by the poor uniformity of the threshold voltage of the source follower transistor of the active pixel circuit.

In some embodiments of the present disclosure, an active pixel sensing device is provided. The active pixel sensing device may be a digital camera, a camcorder, a personal communication system, a game console, a camera for security purposes, a miniature camera for medical purposes, a robot, an X-ray detector, etc. Exemplarily, the active pixel sensing device is an active pixel sensor APS, and the active pixel sensing device includes active pixel circuit(s), a display device, a data processing IC and other electronic accessories.

Figure 10:
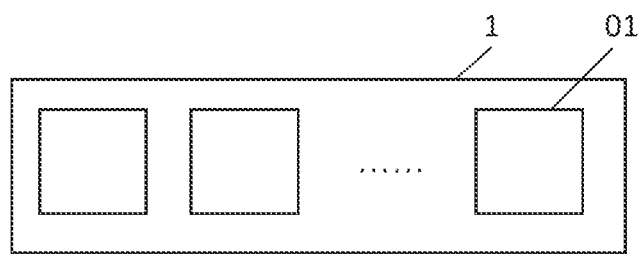
FIG. 10 is a diagram showing a circuit structure of an active pixel sensing device, according to some embodiments of the present disclosure.

In some embodiments, as shown in FIG. 10, the active pixel sensing device 1 includes a plurality of active pixel circuits 01 arranged in an array.

Exemplarily, in an example where the active pixel sensing device is a metal-semiconductor-metal (MSM) X-ray detector, the detector includes an X-ray emitter and an MSM photodetector. The MSM photodetector is provided with a plurality of pixel units arranged in an array therein, and the pixel unit is provided with an active pixel circuit therein. A working principle of the detector is that X-rays emitted by the X-ray emitter pass through a detection object (e.g., a human body) and reach the MSM photodetector, so that the active pixel circuits (specifically, photosensitive devices of the active pixel circuits) in the MSM photodetector generate photo-generated carriers under an irradiation of X-rays, thereby generating currents (i.e., photocurrents). A magnitude of the photocurrent is proportional to a radiation intensity of the X-rays received by the active pixel circuit. Thus, an internal structure of the detection object is obtained according to the magnitude of the photocurrents, and a detection result of the detection object is displayed. Of course, in a case where the X-ray emitter does not emit X-rays, the active pixel circuit will also generate a current under a given voltage, which is called a dark current.

Figure 2:
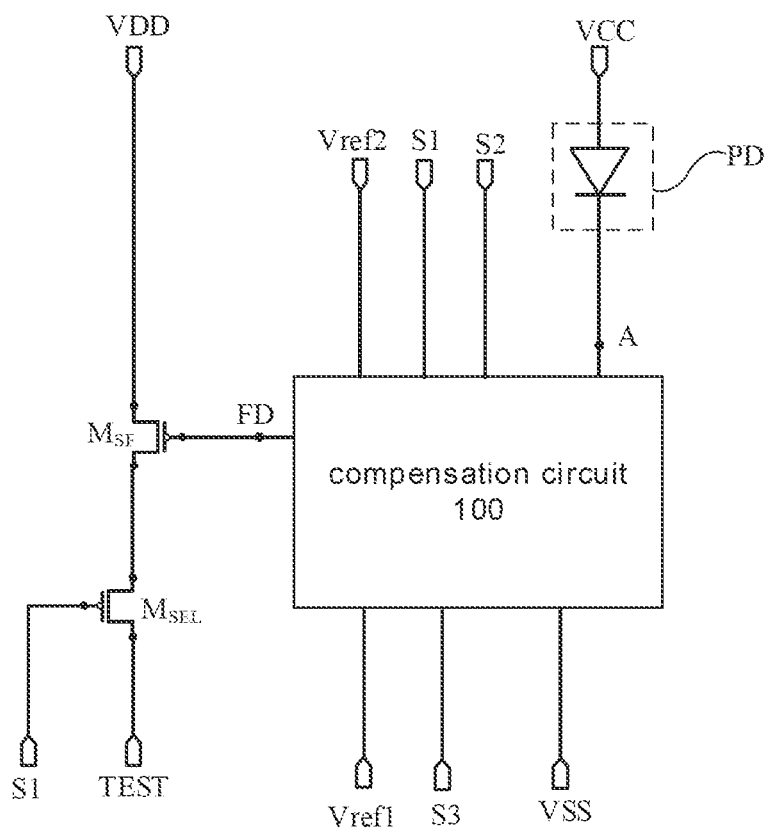
FIG. 2 is a diagram showing a circuit structure of an active pixel circuit, according to some embodiments of the present disclosure.

In some embodiments of the present disclosure, an active pixel circuit 01 is provided. As shown in FIG. 2, the active pixel circuit 01 includes a photosensitive device and a source follower transistor $M_{SF}$. A control electrode of the source follower transistor $M_{SF}$ is coupled to a floating diffusion node FD. The photosensitive device is coupled to a first node A. The photosensitive device is configured to generate a photocurrent under an irradiation of light rays, and to transmit the photocurrent to the first node A, so that a voltage of the first node is associated with a voltage V0 generated by the photocurrent.

As shown in FIG. 2, exemplarily, a photodiode PD may be used as the photosensitive device. The photodiode PD is capable of converting an optical signal into an electrical signal. Exemplarily, an anode of the photodiode PD is coupled to a bias voltage terminal VCC (or a common voltage terminal). For example, a voltage at the bias voltage terminal VCC is 0V. A cathode of the photodiode PD is coupled to the first node A. The photodiode PD generates a photocurrent under an irradiation of light rays, and transmits the photocurrent to the first node A, thereby affecting a voltage at the first node A. The following embodiments are all described by taking an example where the photosensitive device is the photodiode PD.

On this basis, the active pixel circuit 01 further includes a compensation circuit 100.

The compensation circuit 100 is coupled to the first node A. That is, the compensation circuit 100 is coupled to the photosensitive device through the first node A. The compensation circuit 100 is further coupled to the floating diffusion node FD, a first control terminal S1, a second control terminal S2, a third control terminal S3, a first reference voltage terminal Vref1, a second reference voltage terminal Vref2, and a first power supply voltage terminal VSS.

The compensation circuit 100 is configured to: transmit a target threshold voltage Vth' to the first node A under control of voltages of the first control terminal S1, the second control terminal S2, the third control terminal S3, the first reference voltage terminal Vref1, the second reference voltage terminal Vref2, and the first power supply voltage terminal VSS, the voltage of the first node A being associated with the voltage V0 generated by the photocurrent and the target threshold voltage Vth'; store the voltage of the first node A; obtain a compensation voltage V' according to the voltage of the first node A; and output the compensation voltage V to the floating diffusion node FD. The target threshold voltage Vth' is the same as or substantially the same as a threshold voltage Vth of the source follower transistor.

In summary, the active pixel circuit 01 in the embodiments of the present disclosure is capable of transmitting the target threshold voltage Vth' to the first node A through the compensation circuit 100. The voltage of the first node A is associated with the voltage V0 generated by the photocurrent and the target threshold voltage Vth', and the target threshold voltage Vth' is the same as or substantially the same as the threshold voltage Vth of the source follower transistor. That is, the compensation circuit 100 is capable of transmitting the threshold voltage Vth of the source follower transistor to the first node A, so that the voltage of the first node A is associated with the voltage V0 generated by the photocurrent and the threshold voltage Vth of the source follower transistor. Furthermore, the compensation circuit 100 stores the voltage of the first node A, obtains the compensation voltage V according to the voltage of the first node A, and outputs the compensation voltage V to the floating diffusion node FD. In this way, the compensation voltage V is also associated with the voltage V0 generated by the photocurrent and the threshold voltage Vth of the source follower transistor. In a process of controlling a current flowing through the source follower transistor $M_{SF}$ through the compensation voltage V', the threshold voltage Vth of the source follower transistor $M_{SF}$ can be compensated to cancel out the threshold voltage Vth of the source follower transistor $M_{SF}$, so that the current flowing through the source follower transistor $M_{SF}$ is irrelevant to the threshold voltage Vth. Thus, the problem of unstable detection results caused by the threshold voltage Vth of the source follower transistor $M_{SF}$ is avoided, and an accuracy of the detection results of the active pixel circuit 01 is improved.

In some embodiments, as shown in FIG. 2, a selector transistor $M_{SEL}$ is further provided in the active pixel circuit 01. In this case, a first electrode of the source follower transistor $M_{SF}$ is coupled to a second power supply voltage terminal VDD (for example, the second power supply voltage terminal VDD is a high-level power supply voltage terminal that is configured to transmit a DC high-level signal), and a second electrode of the source follower transistor $M_{SF}$ is coupled to a first electrode of the selector transistor $M_{SEL}$. A control electrode of the selector transistor $M_{SEL}$ is coupled to the first control terminal S1, and a second electrode of the selector transistor $M_{SEL}$ is coupled to a signal output terminal TEST. For the active pixel sensing device, the signal output terminal TEST of the active pixel circuit 01 is coupled to the data processing IC (not shown in FIG. 2), to obtain the detection results through the data processing IC.

Specific configurations of the compensation circuit 100 will be further described below.

Figure 3:
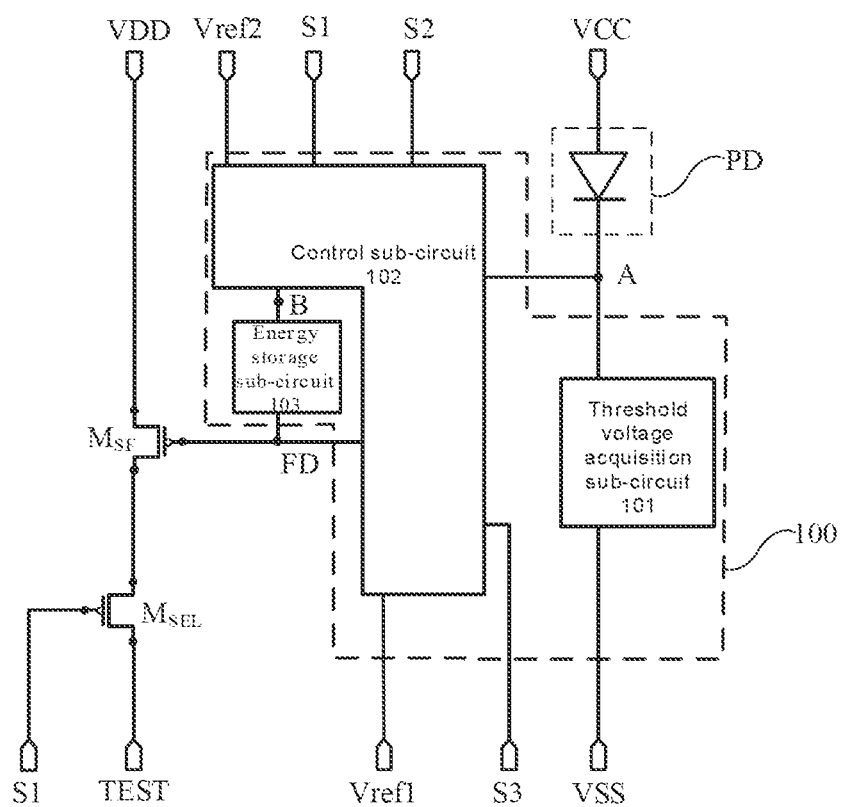
FIG. 3 is a diagram showing a circuit structure of another active pixel circuit, according to some embodiments of the present disclosure.

As shown in FIG. 3, in some embodiments, the compensation circuit 100 may include a threshold voltage acquisition sub-circuit 101, a control sub-circuit 102, and an energy storage sub-circuit 103.

The threshold voltage acquisition sub-circuit 101 is coupled to the first node A and the first power supply voltage terminal VSS (for example, the first power supply voltage terminal VSS is a low-level power supply voltage terminal that is configured to transmit a DC low-level signal). The threshold voltage acquisition sub-circuit 101 is configured to adjust the voltage of the first node A to an associated voltage V1 under the control of a first voltage $V_{SS}$ of the first power supply voltage terminal VSS. The associated voltage V1 is associated with the target threshold voltage Vth' and the voltage V0 generated by the photocurrent.

Figure 4:
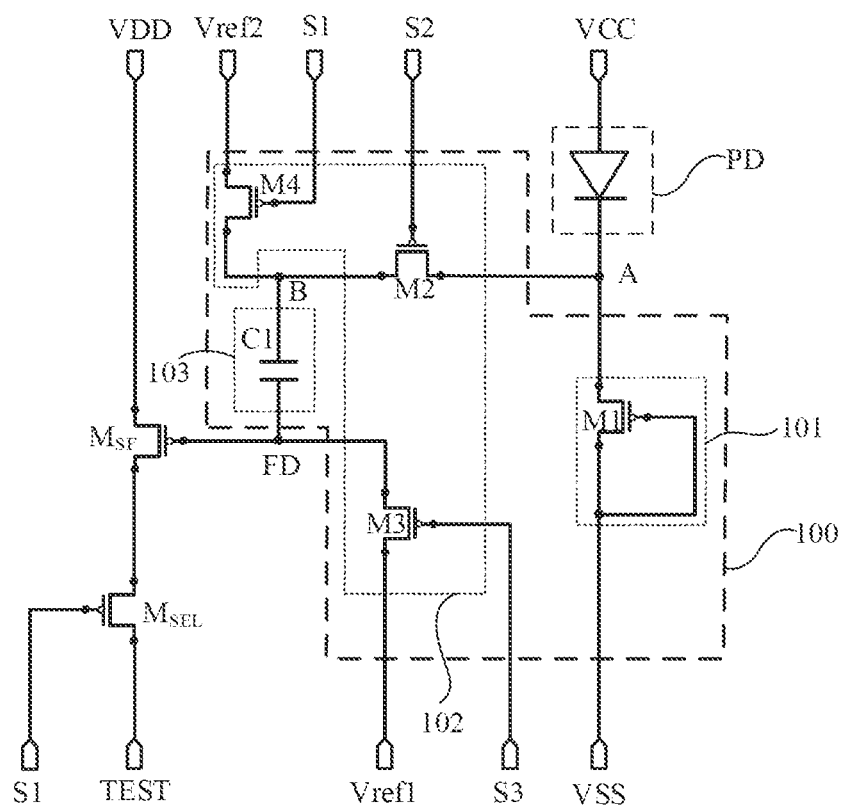
FIG. 4 is a diagram showing a circuit structure of yet another active pixel circuit, according to some embodiments of the present disclosure.

For example, as shown in FIG. 4, the threshold voltage acquisition sub-circuit 101 may include a first transistor M1. A control electrode and a first electrode of the first transistor M1 are coupled to the first power supply voltage terminal VSS, and a second electrode of the first transistor M1 is coupled to the first node A. The first transistor M1 is configured such that the first transistor M1 is turned on under the control of the first voltage $V_{SS}$ of the first power supply voltage terminal VSS and transmits the first voltage $V_{SS}$ received at the first power supply voltage terminal VSS to the first node A.

A threshold voltage of the first transistor M1 is the target threshold voltage Vth'. That is, the threshold voltage of the first transistor M1 is the same as or substantially the same as the threshold voltage Vth of the source follower transistor $M_{SF}$. For example, characteristics of the first transistor M1 are the same as or substantially the same as those of the source follower transistor $M_{SF}$. That is, dimensions, a specification, etc., of the first transistor M1 are the same as those of the source follower transistor $M_{SF}$. For example, a width-to-length ratio of a channel of the first transistor M1 is the same as that of the source follower transistor $M_{SF}$. In an actual layout of a circuit, the first transistor M1 and the source follower transistor $M_{SF}$ are substantially adjacent to each other. In this case, the threshold voltage of the first transistor M1 can be made equal to the threshold voltage Vth of the source follower transistor $M_{SF}$ by setting the dimensions and the specification of the first transistor M1 to be the same as those of the source follower transistor $M_{SF}$.

In this way, the threshold voltage acquisition sub-circuit 101 is capable of adjusting the voltage of the first node A to the associated voltage V1 under the control of the first voltage $V_{SS}$ of the first power supply voltage terminal VSS. The associated voltage V1 is associated with the target threshold voltage Vth' (the threshold voltage Vth of the source follower transistor $M_{SF}$) and the voltage V0 generated by the photocurrent. That is, the voltage of the first node A is the associated voltage $V1=V_{SS}-Vth'-V0=V_{SS}-Vth-V0$. That is, the associated voltage V1 is associated with the threshold voltage Vth of the source follower transistor $M_{SF}$. It should be noted that, as shown in FIG. 4, the photosensitive device being the photodiode PD is taken as an example herein, the anode of the photodiode PD is coupled to the bias voltage terminal VCC, and the cathode of the photodiode PD is coupled to the first node A. In a case where the photodiode PD generates the photocurrent, a potential difference is generated between the anode and cathode (or the cathode and the anode) of the photodiode PD. The potential difference can be considered as the voltage V0 generated by the photocurrent. In a case where the voltage V0 generated by the photocurrent is a positive value, the associated voltage $V1=V_{SS}-Vth+V0$. In a case where the voltage V0 generated by the photocurrent is a negative value, the associated voltage $V1=V_{SS}-Vth-V0$.

The control sub-circuit 102 is coupled to the first node A, a second node B, the floating diffusion node FD, the first control terminal S1, the second control terminal S2, the third control terminal S3, the first reference voltage terminal Vref1 and the second reference voltage terminal Vref2. The energy storage sub-circuit 103 is coupled between the second node B and the floating diffusion node FD.

The control sub-circuit 102 is configured to: output the associated voltage V1 of the first node A and a first reference voltage $V_{ref1}$ received at the first reference voltage terminal Vref1 to the second node B and the floating diffusion node FD respectively under the control of the voltages of the first control terminal S1, the second control terminal S2, and the third control terminal S3; and charge the energy storage sub-circuit 103.

The control sub-circuit 102 is further configured to: adjust a voltage of the second node B from the associated voltage V1 to a second reference voltage $V_{ref2}$ received at the second reference voltage terminal Vref2 under the control of the voltages of the first control terminal S1, the second control terminal S2, and the third control terminal S3; and adjust a voltage of the floating diffusion node FD from the first reference voltage $V_{ref1}$ to the compensation voltage V' through the energy storage sub-circuit 103.

For example, as shown in FIG. 4, the control sub-circuit 102 may include a second transistor M2, a third transistor M3 and a fourth transistor M4.

A control electrode of the second transistor M2 is coupled to the second control terminal S2, a first electrode of the second transistor M2 is coupled to the first node A, and a second electrode of the second transistor M2 is coupled to the second node B. The second transistor M2 is configured such that second transistor M2 is turned on under the control of the second control terminal S2 and transmits the voltage of the first node A to the second node B.

A control electrode of the third transistor M3 is coupled to the third control terminal S3, a first electrode of the third transistor M3 is coupled to the first reference voltage terminal Vref1, and a second electrode of the third transistor M3 is coupled to the floating diffusion node FD. The third transistor M3 is configured such that the third transistor M3 is turned on under the control of the third control terminal S3, and transmits the first reference voltage $V_{ref1}$ received at the first reference voltage terminal Vref1 to the floating diffusion node FD.

A control electrode of the fourth transistor M4 is coupled to the first control terminal S1, a first electrode of the fourth transistor M4 is coupled to the second reference voltage terminal Vref2, and a second electrode of the fourth transistor M4 is coupled to the second node B. The fourth transistor M4 is configured such that the fourth transistor M4 is turned on under the control of the first control terminal S1, and transmits the second reference voltage $V_{ref2}$ received at the second reference voltage terminal Vref2 to the second node B.

The energy storage sub-circuit 103 may include a first capacitor C1. A first electrode of the first capacitor C1 is coupled to the second node B, and a second electrode of the first capacitor C1 is coupled to the floating diffusion node FD.

Figure 5:
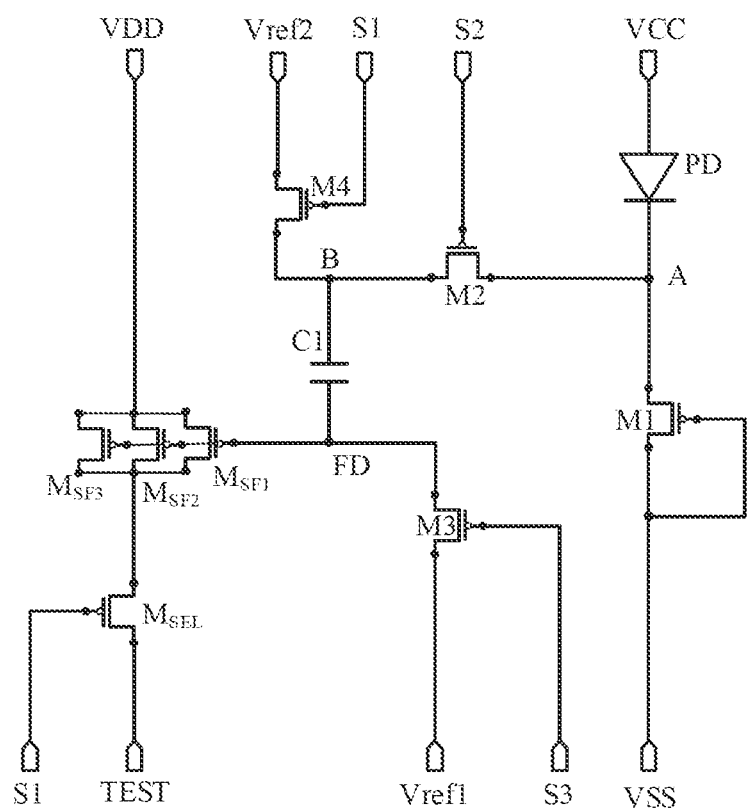
FIG. 5 is a diagram showing a circuit structure of yet another active pixel circuit, according to some embodiments of the present disclosure.

On this basis, in order to increase an amplification ratio of the active pixel circuit 01, in some embodiments, the active pixel circuit 01 further includes a plurality of transistors in parallel with the source follower transistor. Characteristics of the plurality of transistors are the same as or substantially the same as characteristics of the source follower transistor. For example, the plurality of transistors are also referred to as source follower transistors. That is, as shown in FIG. 5, a plurality of source follower transistors in parallel (such as $M_{SF1}$, $M_{SF2}$, $M_{SF3}$) are provided in the active pixel circuit 01. A control electrode of each of the plurality of source follower transistors in parallel is coupled to the floating diffusion node, a first electrode of each of the plurality of source follower transistors in parallel is coupled to the second power supply voltage terminal VDD, and a second electrode of each of the plurality of source follower transistors in parallel is coupled to the signal output terminal TEST.

In addition, characteristics of the plurality of source follower transistors in parallel are the same. That is, sizes, specifications, etc., of the plurality of source follower transistors in parallel are the same. In an actual layout of a circuit, the plurality of source follower transistors in parallel are substantially adjacent to each other. That is, threshold voltages of the plurality of source follower transistors in parallel are equal. In this case, the amplification ratio of the active pixel circuit 01 can be increased by a corresponding multiple according to the number of the source follower transistors in parallel. For example, the amplification ratio in a case where two source follower transistors in parallel are provided will be twice the amplification ratio in a case where one source follower transistor is provided.

It should be noted that FIG. 5 is only exemplarily described by taking three source follower transistors in parallel ($M_{SF1}$, $M_{SF2}$, $M_{SF3}$) as an example, but the present disclosure is not limited to this. Two, four, or five source follower transistors in parallel can also be provided.

As shown in FIGS. 4 and 5, a specific structure of the active pixel circuit in some embodiments of the present disclosure will be integrally and exemplarily introduced below.

As shown in FIG. 4, the compensation circuit 100 includes the threshold voltage acquisition sub-circuit 101, the control sub-circuit 102, and the energy storage sub-circuit 103. The threshold voltage acquisition sub-circuit 101 includes the first transistor M1. The control sub-circuit 102 includes the second transistor M2, the third transistor M3, and the fourth transistor M4. The energy storage sub-circuit 103 includes the first capacitor C1. The active pixel circuit 101 further includes the selector transistor. The photosensitive device is the photodiode PD.

The control electrode of the source follower transistor $M_{SF}$ is coupled to the floating diffusion node FD, the first electrode of the source follower transistor $M_{SF}$ is coupled to the second power supply voltage terminal VDD, and the second electrode of the source follower transistor $M_{SF}$ is coupled to the first electrode of the selector transistor $M_{SEL}$. The control electrode of the selector transistor $M_{SEL}$ is coupled to the first control terminal S1, and the second electrode of the selector transistor $M_{SEL}$ is coupled to the signal output terminal TEST. The source follower transistor $M_{SF}$ is configured to transmit a second voltage $V_{DD}$ received at the second power supply voltage terminal VDD to the first electrode of the selector transistor $M_{SEL}$ under control of the voltage of the floating diffusion node FD. The selector transistor $M_{SEL}$ is configured to transmit a voltage signal of the first electrode of the selector transistor $M_{SEL}$ to the signal output terminal TEST under the control of the voltage of the first control terminal S1.

The control electrode and the first electrode of the first transistor M1 are coupled to the first power supply voltage terminal VSS, and the second electrode of the first transistor M1 is coupled to the first node A. The first transistor M1 is configured such that the first transistor M1 is turned on under the control of the first voltage $V_{SS}$ of the first power supply voltage terminal VSS, and transmits the first voltage $V_{SS}$ received at the first power supply voltage terminal VSS to the first node A.

The control electrode of the second transistor M2 is coupled to the second control terminal S2, the first electrode of the second transistor M2 is coupled to the first node A, and the second electrode of the second transistor M2 is coupled to the second node B. The second transistor M2 is configured such that the second transistor M2 is turned on under the control of the second control terminal S2, and transmits the voltage of the first node A to the second node B.

The control electrode of the third transistor M3 is coupled to the third control terminal S3, the first electrode of the third transistor M3 is coupled to the first reference voltage terminal Vref1, and the second electrode of the third transistor M3 is coupled to the floating diffusion node FD. The third transistor M3 is configured such that the third transistor M3 is turned on under the control of the third control terminal S3, and transmits the first reference voltage $V_{ref1}$ received at the first reference voltage terminal Vref1 to the floating diffusion node FD.

The control electrode of the fourth transistor M4 is coupled to the first control terminal S1, the first electrode of the fourth transistor M4 is coupled to the second reference voltage terminal Vref2, and the second electrode of the fourth transistor M4 is coupled to the second node B. The fourth transistor M4 is configured such that the fourth transistor M4 is turned on under the control of the first control terminal S1, and transmits the second reference voltage $V_{ref2}$ received at the second reference voltage terminal Vref2 to the second node B.

The first electrode of the first capacitor C1 is coupled to the second node B, and the second electrode of the first capacitor C1 is coupled to the floating diffusion node FD.

The anode of the photodiode PD is coupled to the bias voltage terminal VCC, and the cathode of the photodiode PD is coupled to the first node A.

It should be noted that in the circuits in the embodiments of the present disclosure, the first node A, the second node B and the floating diffusion node FD do not represent actual components, but rather represent junctions of related electrical connections in the circuit diagrams. That is, these nodes are nodes equivalent to the junctions of the related electrical connections in the circuit diagrams.

Hereinafter, a method for controlling the active pixel circuit 01 shown in FIG. 4 will be described.

Figure 6:
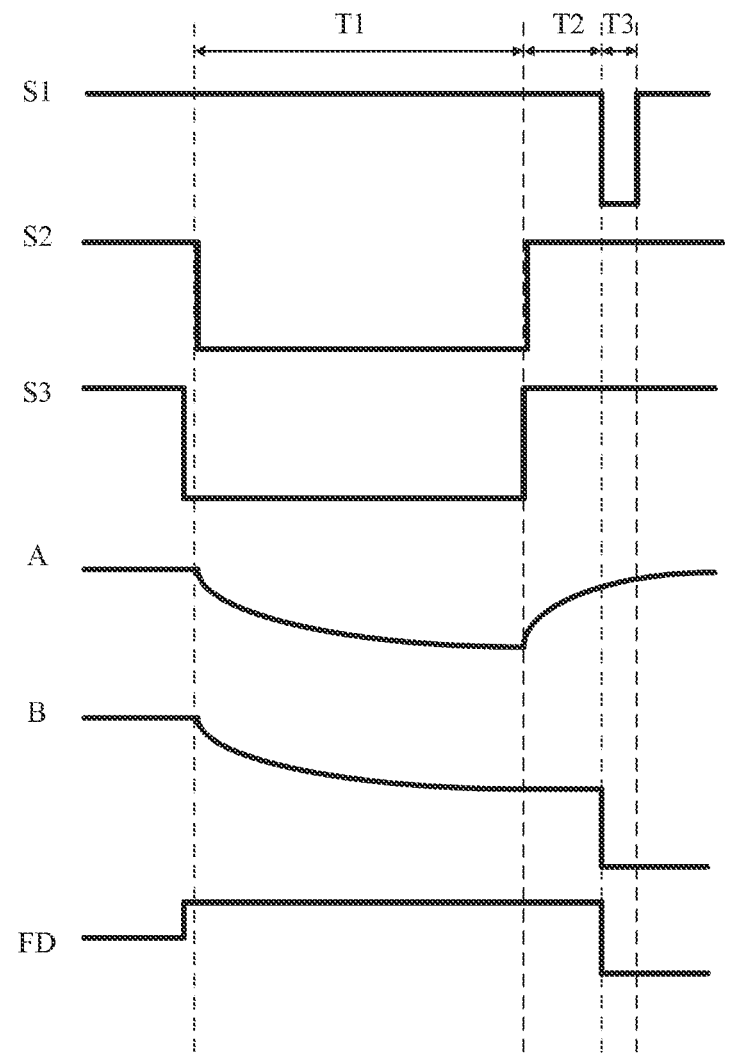
FIG. 6 is a control timing diagram of an active pixel circuit, according to some embodiments of the present disclosure.

As shown in FIG. 6, the method for controlling the active pixel circuit 01 includes a first stage T1, a second stage T2, and a third stage T3.

Exemplarily, in three stages of the first stage T1, the second stage T2 and the third stage T3, the first power supply voltage terminal VSS transmits the low-level power supply voltage $V_{SS}$, the second power supply voltage terminal VDD transmits the high-level power supply voltage $V_{DD}$, the first reference voltage terminal Vref1 transmits the first reference voltage $V_{ref1}$, and the second reference voltage terminal Vref2 transmits the second reference voltage $V_{ref2}$. In the three stages, there is always a current from the photodiode PD to the first power supply voltage terminal VSS. That is, the first transistor is in a turn-on state in the three stages under the control of the low-level power supply voltage $V_{SS}$ transmitted by the first power supply voltage terminal VSS.

In the first stage T1 (also called a lighting stage):

The photodiode PD (the photosensitive device) generates the photocurrent under the irradiation of light rays, and transmits the photocurrent to the first node A; the threshold voltage acquisition sub-circuit 101 adjusts the voltage of the first node A to the associated voltage V1, the associated voltage V1 being associated with the target threshold voltage Vth' and the voltage V0 generated by the photocurrent.

A turn-off voltage is input to the first control terminal S1, and turn-on voltages are respectively input to the second control terminal S2 and the third control terminal S3. The control sub-circuit 102 outputs the associated voltage V1 of the first node A to the second node B, outputs the first reference voltage $V_{ref1}$ of the reference voltage terminal Vref1 to the floating diffusion node FD, and charges the energy storage sub-circuit 103.

It should be noted that the turn-off voltage refers to a voltage that makes a transistor that is controlled by the turn-off voltage be cut off, and the turn-on voltage refers to a voltage that makes a transistor that is controlled by the turn-on voltage conductive. Exemplarily, in a case where the transistors included in the active pixel circuit 01 in the embodiments of the present disclosure are all P-type transistors, the turn-off voltage is a high-level voltage, and the turn-on voltage is a low-level voltage. This description is also applicable to the contents mentioned below.

Figure 7:
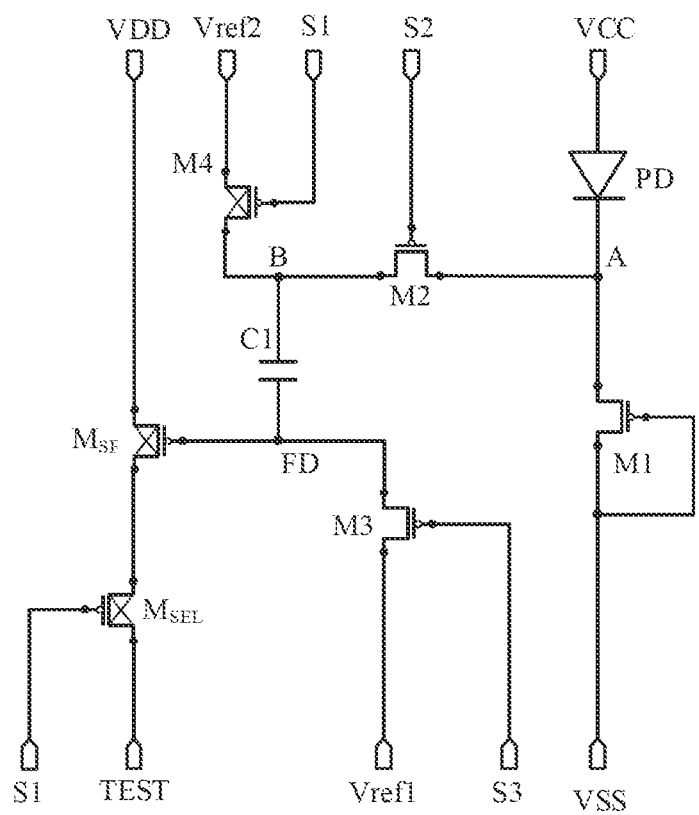
FIG. 7 is a working schematic diagram of an active pixel circuit in a first stage, according to some embodiments of the present disclosure.

Exemplarily, referring to FIGS. 6 and 7, the threshold voltage of the first transistor M1 is the target threshold voltage Vth', and the threshold voltage of the first transistor M1 is the same as the threshold voltage Vth of the source follower transistor $M_{SF}$. In the first stage T1, the photodiode PD generates the photocurrent under the irradiation of light rays, and transmits the photocurrent to the first node A. The voltage generated by the photocurrent is V0. At a same time, the first transistor M1 transmits the first voltage $V_{SS}$ received at the first power supply voltage terminal VSS from the first electrode to the second electrode thereof under drive of the low-level power supply voltage $V_{SS}$ of the first power supply voltage terminal VSS, so that the voltage of the first node A is associated with the target threshold voltage Vth' (the threshold voltage Vth of the source follower transistor $M_{SF}$) and the voltage V0 generated by the photocurrent, and the voltage of the first node A is the associated voltage V1=$V_{SS}$−V0−Vth.

In addition, the fourth transistor M4 and the selector transistor $M_{SEL}$ are turned off under control of the high-level voltage input from the first control terminal S1. The second transistor M2 is turned on under control of the low-level voltage input from the second control terminal S2, and transmits the voltage of the first node A to the second node B. The third transistor M3 is turned on under control of the low-level voltage input from the third control terminal S3, and transmits the first reference voltage $V_{ref1}$ received at the first reference voltage terminal Vref1 to the floating diffusion node FD.

Therefore, in this case, the voltage of the second node B is equal to the voltage of the first node A, and is $[V_{SS}-V0-Vth]$. The voltage of the floating diffusion node FD is equal to the first reference voltage $V_{ref1}$ of the first reference voltage terminal Vref1. The first capacitor C1 is charged through a voltage difference between the second node B and the floating diffusion node FD, and the voltage difference across the first capacitor C1 is $[V_{SS}-V0-Vth-V_{ref1}]$.

In the second stage T2 (also called a dark state stage):

Turn-off voltages are respectively input to the first control terminal S1, the second control terminal S2 and the third control terminal S3. The control sub-circuit 100 maintains the voltage of the second node B at the associated voltage V1, and maintains the voltage of the floating diffusion node FD at the first reference voltage $V_{ref1}$.

Figure 8:
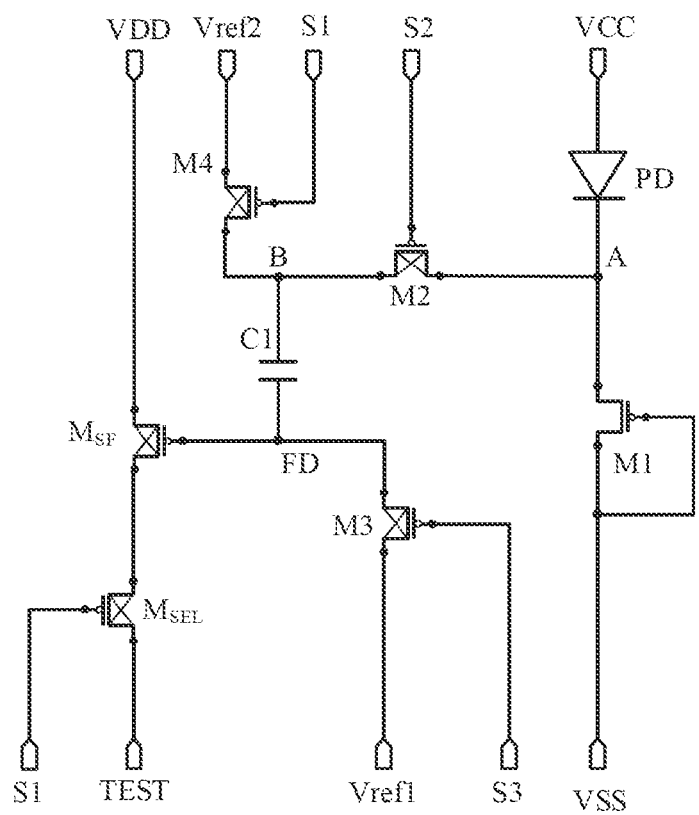
FIG. 8 is a working schematic diagram of an active pixel circuit in a second stage, according to some embodiments of the present disclosure.

Exemplarily, referring to FIGS. 6 and 8, the fourth transistor M4, the selector transistor $M_{SEL}$, the second transistor M2 and the third transistor M3 are all turned off under control of the high-level voltages input from the first control terminal S1, the second control terminal S2, and the third control terminal S3. The voltage of the second node B is maintained at the associated voltage V1, and the voltage of the floating diffusion node FD is maintained at the first reference voltage $V_{ref1}$. An amount of charges stored in the first capacitor C1 remains unchanged. That is, the voltage difference across the first capacitor C1 is still $[V_{SS}-V0-Vth-V_{ref1}]$.

In the third stage T3 (also called a read stage):

A turn-on voltage is input to the first control terminal S1, and turn-off voltages are respectively input to the second control terminal S2 and the third control terminal S3 continuously. The control sub-circuit 102 adjusts the voltage of the second node B from the associated voltage V1 to the second reference voltage $V_{ref2}$ received at the second reference voltage terminal Vref2, and adjusts the voltage of the floating diffusion node FD from the first reference voltage $V_{ref1}$ to the compensation voltage V' through the energy storage sub-circuit 103.

Figure 9:
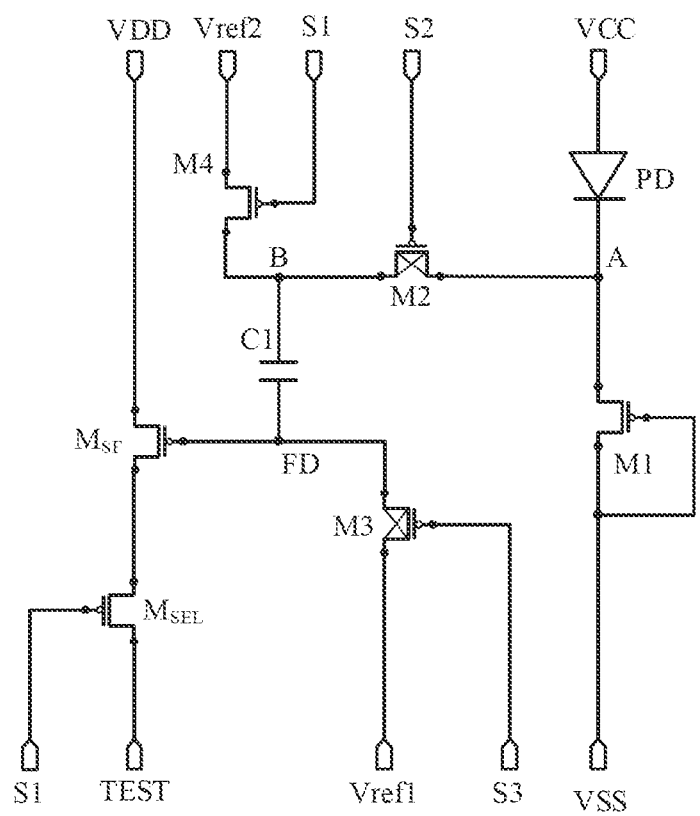
FIG. 9 is a working schematic diagram of an active pixel circuit in a third stage, according to some embodiments of the present disclosure.

Exemplarily, referring to FIGS. 6 and 9, the high-level voltages are respectively input to the second control terminal S2 and the third control terminal S3 continuously, so that the second transistor M2 and the third transistor M3 are kept turned off. The low-level voltage is input to the first control terminal S1, so that the fourth transistor M4 and the selector transistor $M_{SEL}$ are turned on. Thus, the fourth transistor M4 transmits the second reference voltage $V_{ref2}$ received at the second reference voltage terminal Vref2 to the second node B, so that the voltage of the second node B is adjusted from the associated voltage $V1=V_{SS}-V0-Vth$ to the second reference voltage $V_{ref2}$ of the second reference voltage terminal Vref2. That is, a voltage of the first electrode (i.e., the electrode coupled to the second node B) of the first capacitor C1 changes from the associated voltage V1 to the second reference voltage $V_{ref2}$, and a voltage change is $[V_{ref2}-(V_{SS}-V0-Vth)]$.

According to the law of conservation of charge, it is impossible for the charges stored in the first capacitor C1 to change suddenly. Therefore, a voltage of the second electrode (that is, the electrode coupled to the floating diffusion node FD) of the first capacitor C1 will undergo a same voltage change. In this case, the voltage of the floating diffusion node FD is adjusted from the first reference voltage $V_{ref1}$ in the second stage T2 to the compensation voltage $V'=V_{ref1}+V_{ref2}-V_{SS}+V0+Vth$. The control electrode of the source follower transistor $M_{SF}$ is coupled to the floating diffusion node FD, and thus a voltage of the control electrode of the source follower transistor $M_{SF}$ is also $V'=V_{ref1}+V_{ref2}-V_{SS}+V0+Vth$.

For a transistor, in a turn-on state, a magnitude of a current $I_{on}$ flowing through the transistor is associated with $(V_{GS}-Vth)$, i.e., $I_{on}=\beta(V_{GS}-Vth)^2$, in which $V_{GS}$ is a gate-source voltage difference of the transistor, Vth is a threshold voltage of the transistor, and $\beta$ is an intrinsic conductivity factor of the transistor, which is a constant value. In this case, as shown in FIG. 9, in the active pixel circuit 01, the current flowing through the source follower transistor $M_{SF}$ is $I=\beta(V_{GS}-Vth)^2=\beta(V_{ref1}+V_{ref2}-V_{SS}+V0+Vth-V_{DD}-Vth)^2=\beta(V_{ref1}+V_{ref2}-V_{SS}+V_{DD})^2$, which is a current I output through the signal output terminal TEST. Where β is an intrinsic conductivity factor of the source follower transistor $M_{SF}$. It can be seen from this formula that the current I output through the signal output terminal TEST is irrelevant to the threshold voltage Vth of the source follower transistor $M_{FS}$. In addition, the compensation circuit is provided in the active pixel circuit 01 in some embodiments of the present disclosure, that is, the threshold voltage Vth of the source follower transistor $M_{SF}$ is compensated. Therefore, the problem of unstable detection results caused by the threshold voltage Vth of the source follower transistor may be avoided, and the accuracy of the detection results of the active pixel circuit 01 is improved.

It should be noted that the transistors may be enhancement transistors, or depletion transistors. The first electrode of the transistor may be a source, and the second electrode of the transistor may be a drain, or the first electrode of the transistor may be a drain, and the second electrode of the transistor may be a source, which is not limited in the present disclosure.

In the embodiments of the present disclosure, conducting (turn-on) and non-conducting (turn-off) processes of the transistors are described by taking an example where all transistors are P-type transistors. In the embodiments of the present disclosure, the transistors may also be N-type transistors. In a case where all transistors are N-type transistors, each control signal needs to be inverted.

A person of ordinary skill in the art will understand that, all or part of the steps in the above method embodiments may be implemented by using hardware related to program instructions. The program instructions may be stored in a computer-readable storage medium for performing the steps included in the above method embodiments. The storage media include various media capable of storing program codes, such as a read-only memory (ROM), a random-access memory (RAM), a magnetic disk, or an optical disk.

The forgoing descriptions are merely specific implementations of the present disclosure, but the protection scope of the present disclosure is not limited thereto. Any changes or replacements those skilled in the art could conceive of within the technical scope of the present disclosure shall be included in the protection scope of the present disclosure. Therefore, the protection scope of the present disclosure shall be subject to the protection scope of the claims.

What is claimed is:

1. An active pixel circuit, comprising:
   a photosensitive device coupled to a first node, the photosensitive device being configured to generate a photocurrent under an irradiation of light rays, and transmit the photocurrent to the first node;
   a source follower transistor, a control electrode of the source follower transistor being coupled to a floating diffusion node; and a compensation circuit coupled to the first node, and further coupled to the floating diffusion node, a first control terminal, a second control terminal, a third control terminal, a first reference voltage terminal, a second reference voltage terminal, and a first power supply voltage terminal, wherein the compensation circuit is configured to: transmit a target threshold voltage to the first node under control of voltages of the first control terminal, the second control terminal, the third control terminal, the first reference voltage terminal, the second reference voltage terminal, and the first power supply voltage terminal, a voltage of the first node being associated with a voltage generated by the photocurrent and the target threshold voltage;

store the voltage of the first node; obtain a compensation voltage according to the voltage of the first node; and output the compensation voltage to the floating diffusion node, wherein the target threshold voltage is the same as a threshold voltage of the source follower transistor;

wherein the compensation circuit includes a threshold voltage acquisition sub-circuit, a control sub-circuit, and an energy storage sub-circuit;

the threshold voltage acquisition sub-circuit is coupled to the first node and the first power supply voltage terminal;

the control sub-circuit is coupled to the first node, a second node, the floating diffusion node, the first control terminal, the second control terminal, the third control terminal, the first reference voltage terminal, and the second reference voltage terminal;

the energy storage sub-circuit is coupled between the second node and the floating diffusion node;

the threshold voltage acquisition sub-circuit is configured to adjust a voltage of the first node to an associated voltage under control of a voltage of the first power supply voltage terminal, wherein the associated voltage is associated with the target threshold voltage and the voltage generated by the photocurrent;

the control sub-circuit is configured to: output the associated voltage of the first node to the second node and a first reference voltage received at the first reference voltage terminal to the floating diffusion node under control of voltages of the first control terminal, the second control terminal, and the third control terminal; and charge the energy storage sub-circuit;

the control sub-circuit is further configured to: adjust a voltage of the second node from the associated voltage to a second reference voltage received at the second reference voltage terminal under the control of the voltages of the first control terminal, the second control terminal, and the third control terminal; and adjust a voltage of the floating diffusion node from the first reference voltage to the compensation voltage through the energy storage sub-circuit.

2. The active pixel circuit according to claim 1, wherein the threshold voltage acquisition sub-circuit includes a first transistor;

a control electrode and a first electrode of the first transistor are coupled to the first power supply voltage terminal, and a second electrode of the first transistor is coupled to the first node;

a threshold voltage of the first transistor is the target threshold voltage.

3. The active pixel circuit according to claim 2, wherein the control sub-circuit includes a second transistor, a third transistor and a fourth transistor;

a control electrode of the second transistor is coupled to the second control terminal, a first electrode of the second transistor is coupled to the first node, and a second electrode of the second transistor is coupled to the second node;

a control electrode of the third transistor is coupled to the third control terminal, a first electrode of the third transistor is coupled to the first reference voltage terminal, and a second electrode of the third transistor is coupled to the floating diffusion node;

a control electrode of the fourth transistor is coupled to the first control terminal, a first electrode of the fourth transistor is coupled to the second reference voltage terminal, and a second electrode of the fourth transistor is coupled to the second node.

4. The active pixel circuit according to claim 3, wherein the energy storage sub-circuit includes a first capacitor;

a first electrode of the first capacitor is coupled to the second node, and a second electrode of the first capacitor is coupled to the floating diffusion node.

5. The active pixel circuit according to claim 4, further comprising a plurality of transistors in parallel with the source follower transistor, characteristics of the plurality of transistors being the same as characteristics of the source follower transistor.

6. The active pixel circuit according to claim 5, further comprising a selector transistor;

a first electrode of the source follower transistor is coupled to a second power supply voltage terminal, and a second electrode of the source follower transistor is coupled to a first electrode of the selector transistor;

a control electrode of the selector transistor is coupled to the first control terminal, and a second electrode of the selector transistor is coupled to a signal output terminal.

7. The active pixel circuit according to claim 1, wherein the photosensitive device is a photodiode, an anode of the photodiode is coupled to a bias voltage terminal, and a cathode of the photodiode is coupled to the first node.

8. The active pixel circuit according to claim 1, wherein the compensation circuit includes a threshold voltage acquisition sub-circuit, a control sub-circuit, and an energy storage sub-circuit; the threshold voltage acquisition sub-circuit includes a first transistor;

the control sub-circuit includes a second transistor, a third transistor and a fourth transistor;

the energy storage sub-circuit includes a first capacitor;

the active pixel circuit further includes a selector transistor; the photosensitive device is a photodiode;

a control electrode and a first electrode of the first transistor are coupled to the first power supply voltage terminal, and a second electrode of the first transistor is coupled to the first node;

a control electrode of the second transistor is coupled to the second control terminal, a first electrode of the second transistor is coupled to the first node, and a second electrode of the second transistor is coupled to a second node;

a control electrode of the third transistor is coupled to the third control terminal, a first electrode of the third transistor is coupled to the first reference voltage terminal, and a second electrode of the third transistor is coupled to the floating diffusion node;

a control electrode of the fourth transistor is coupled to the first control terminal, a first electrode of the fourth transistor is coupled to the second reference voltage terminal, and a second electrode of the fourth transistor is coupled to the second node;

a first electrode of the first capacitor is coupled to the second node, and a second electrode of the first capacitor is coupled to the floating diffusion node;

a first electrode of the source follower transistor is coupled to a second power supply voltage terminal, and a second electrode of the source follower transistor is coupled to a first electrode of the selector transistor;

a control electrode of the selector transistor is coupled to the first control terminal, and a second electrode of the selector transistor is coupled to a signal output terminal;

an anode of the photodiode is coupled to a bias voltage terminal, and a cathode of the photodiode is coupled to the first node.

9. A method for controlling the active pixel circuit according to claim 1, the compensation circuit of the active pixel circuit includes a threshold voltage acquisition sub-circuit, a control sub-circuit, and an energy storage sub-circuit, the method for controlling the active pixel circuit includes:

in a first stage:
the photosensitive device generating the photocurrent under the irradiation of light rays, and transmitting the photocurrent to the first node;

providing a voltage to a first power supply voltage terminal, so that the threshold voltage acquisition sub-circuit adjusts a voltage of the first node to an associated voltage under the control of the voltage of the first power supply voltage terminal, wherein the associated voltage is associated with the target threshold voltage and the voltage generated by the photocurrent;

providing a turn-off voltage to the first control terminal, and turn-on voltages respectively to the second control terminal and the third control terminal, so that the control sub-circuit outputs the associated voltage of the first node to a second node, and a first reference voltage received at the first reference voltage terminal to the floating diffusion node under control of voltages of the first control terminal, the second control terminal, and the third control terminal, and charges the energy storage sub-circuit;

in a second stage:
providing turn-off voltages respectively to the first control terminal, the second control terminal and the third control terminal, so that the control sub-circuit maintains a voltage of the second node at the associated voltage and maintains a voltage of the floating diffusion node at the first reference voltage under control of voltages of the first control terminal, the second control terminal and the third control terminal;

in a third stage:
providing a turn-on voltage to the first control terminal, and turn-off voltages respectively to the second control terminal and the third control terminal, so that the control sub-circuit adjusts the voltage of the second node from the associated voltage to a second reference voltage received at the second reference voltage terminal under control of voltages of the first control terminal, the second control terminal, and the third control terminal, and adjusts the voltage of the floating diffusion node from the first reference voltage to the compensation voltage through the energy storage sub-circuit.

10. An active pixel sensing device, comprising at least one active pixel circuit according to claim 1.

11. The active pixel sensing device according to claim 10, wherein the at least one active pixel circuit includes a plurality of active pixel circuits arranged in an array.

12. The active pixel circuit according to claim 1, wherein the control sub-circuit includes a second transistor, a third transistor and a fourth transistor;

a control electrode of the second transistor is coupled to the second control terminal, a first electrode of the second transistor is coupled to the first node, and a second electrode of the second transistor is coupled to the second node;

a control electrode of the third transistor is coupled to the third control terminal, a first electrode of the third transistor is coupled to the first reference voltage terminal, and a second electrode of the third transistor is coupled to the floating diffusion node;

a control electrode of the fourth transistor is coupled to the first control terminal, a first electrode of the fourth transistor is coupled to the second reference voltage terminal, and a second electrode of the fourth transistor is coupled to the second node.

13. The active pixel circuit according to claim 1, wherein the energy storage sub-circuit includes a first capacitor;

a first electrode of the first capacitor is coupled to the second node, and a second electrode of the first capacitor is coupled to the floating diffusion node.

14. The active pixel circuit according to claim 1, further comprising a plurality of transistors in parallel with the source follower transistor, characteristics of the plurality of transistors being the same as characteristics of the source follower transistor.

15. The active pixel circuit according to claim 1, further comprising a selector transistor;

a first electrode of the source follower transistor is coupled to a second power supply voltage terminal, and a second electrode of the source follower transistor is coupled to a first electrode of the selector transistor;

a control electrode of the selector transistor is coupled to the first control terminal, and a second electrode of the selector transistor is coupled to a signal output terminal.

* * * * *